(12) United States Patent
Konzelmann et al.

(10) Patent No.: US 7,614,310 B2
(45) Date of Patent: *Nov. 10, 2009

(54) ULTRASOUND FLOW SENSOR WITH A MODULO-2PI FOR A REMAINING PART TRACING

(75) Inventors: Uwe Konzelmann, Asperg (DE); Tobias Lang, Stuttgart (DE); Sami Radwan, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 154 days.

This patent is subject to a terminal disclaimer.

(21) Appl. No.: 11/576,284

(22) PCT Filed: Dec. 6, 2005

(86) PCT No.: PCT/EP2005/056520

§ 371 (c)(1),
(2), (4) Date: Mar. 29, 2007

(87) PCT Pub. No.: WO2006/081887

PCT Pub. Date: Aug. 10, 2006

(65) Prior Publication Data

US 2008/0250868 A1    Oct. 16, 2008

(30) Foreign Application Priority Data

Jan. 31, 2005  (DE) .................... 10 2005 004 331

(51) Int. Cl.
*G01F 1/66* (2006.01)

(52) U.S. Cl. .................................................. 73/861.27
(58) Field of Classification Search ............. 73/861.27, 73/861.18
See application file for complete search history.

(56) References Cited

U.S. PATENT DOCUMENTS

| 5,046,500 A | 9/1991 | Fehr |
| 6,062,091 A | 5/2000 | Baumoel |

FOREIGN PATENT DOCUMENTS

| DE | 198 18 053 | 10/1998 |
| EP | 0 338 593 | 10/1989 |
| EP | 0 362 631 | 4/1990 |
| WO | 00/43736 | 7/2000 |

OTHER PUBLICATIONS

U.S. Appl. No. 12/042,369, filed Mar. 5, 2008, Zang et al.*

* cited by examiner

*Primary Examiner*—Jewel Thompson
(74) *Attorney, Agent, or Firm*—Michael J. Striker

(57) ABSTRACT

For determining the transit time of an ultrasonic signal from an ultrasonic sensor that was launched into a measurement path by an ultrasonic converter, the phase shift of the ultrasonic signal is determined relative to a reference timing signal, and a remainder is determined as a measure of the transit time of the ultrasonic signal so that the phase shift is determined using a quadrature demodulation scheme, with which the received ultrasonic signal is inverted, in a segmented manner, using a timing signal and a phase-shifted timing signal, and the remainder is determined based on a characteristic quantity of the ultrasonic signal.

17 Claims, 4 Drawing Sheets

ULTRASOUND FLOW SENSOR WITH A MODULO-2PI FOR A REMAINING PART TRACING

CROSS-REFERENCE TO A RELATED APPLICATION

The invention described and claimed hereinbelow is also Described in German Patent Application DE 10 2005 004 331.3 filed on Jan. 31, 2005. This German Patent Application provides the basis for a claim of priority of invention under 35 U.S.C. 119(a)-(d).

BACKGROUND OF THE INVENTION

The present invention relates to a method for determining the transit time of an ultrasonic signal from an ultrasonic flow sensor, and to an ultrasonic flow senor.

Ultrasonic flow sensors are used, in particular, to measure the volume flow, mass flow, or the flow rate of a gaseous or liquid medium flowing through a pipeline. A known type of ultrasonic flow sensor includes two ultrasonic converters located such that they are offset in the direction of flow, each of which generates ultrasonic signals and transmits them to the other ultrasonic converter. The ultrasonic signals are received by the other converter and are evaluated using electronics. The difference between the transit time of the signal in the direction of flow and the transit time of the signal in the opposite direction is a measure of the flow rate of the fluid.

FIG. 1 shows a typical design of an ultrasonic flow sensor with two ultrasonic converters A, B, which are located inside a pipeline 3 and are diametrically opposed at a distance L from each other. A fluid 1 flows in pipeline 3 with a velocity v in the direction of arrow 2. Measurement path L is tilted relative to flow direction 2 at an angle α. While a measurement is being carried out, ultrasonic converters A, B send ultrasonic pulses to each other. The signals are decelerated or accelerated, depending on the direction of the flow. The transit times of the ultrasonic signals are a measure of the flow rate to be determined.

FIG. 2 shows a greatly simplified schematic depiction of the electrical circuit of the system in FIG. 1. The two ultrasonic converters A, B are connected with control and evaluation electronics 4 and are activated by an oscillator with a specified clock frequency 8 (square-wave signal). Ultrasonic signals 15 generated as a result (only envelope 16 of ultrasonic signals 15 is shown here) travel along measurement path L and are detected by the other ultrasonic converter A, B. Transit time $t_{12}$ or $t_{21}$ of signals 15 is measured.

To measure the transit time of an ultrasonic signal 15, it is essential that the instant of receipt of ultrasonic signal 15 be determined unequivocally and exactly. Different events can be defined as the instant of receipt of an ultrasonic signal. It is known from the related art, e.g., to define the first zero crossing $N_0$ of ultrasonic signal 15 after the signal amplitude has exceeded a specified threshold as the "instant of receipt". As an alternative, e.g., the instant at which the maximum amplitude or centroid $t_s$ of envelope 16 of ultrasonic signals 15 occurs can be defined as the instant of receipt. It is also known to determine the transit time of ultrasonic signal 15 by evaluating the phase of the signal relative to reference timing signal 8. Conventional methods for determining transit time are typically relatively complex or they are not sufficiently robust against interfering signals.

SUMMARY OF THE INVENTION

The object of the present invention, therefore, is to provide a method for determining the transit time of an ultrasonic signal in an ultrasonic flow sensor, and to provide an ultrasonic flow sensor with a special signal evaluation that is particularly easy to realize and is highly robust against interferences.

One of the main ideas behind the present invention is to determine the phase angle (Δφ) of an ultrasonic signal relative to a reference timing signal using a quadrature demodulation scheme, to calculate the remaining transit time for the ultrasonic signal based on the phase angle (Δφ), and to calculate a remainder (r(t)), which is a whole-number multiple of 2 pi. To determine the phase angle (Δφ), the ultrasonic signal is inverted in a segmented manner using a timing signal and a phase-shifted timing signal. The signals that have been inverted in a segmented manner are then preferably integrated or filtered, and the phase angle (Δφ) is determined using a trigonometric calculation. The remainder (r(t)) is determined, according to the present invention, based on a specified reception event of the ultrasonic signal, e.g., the instant of receipt of the centroid of an envelope. A particular advantage of quadrature demodulation is that this technique serves as a particularly narrow-banded filter against interfering signals, but without resulting in a phase shift of the signal. Conventional band-pass filtering with RC elements would cause, e.g., a phase shift, which would drift with temperature. This could potentially result in errors in the transit time measurement. Despite the extraordinary robustness of the quadrature demodulation scheme against interfering signals, the amount of hardware required therefor is relatively small compared to methods that are equally robust, e.g., cross correlation.

The reception event of the ultrasonic signal, based on which the remainder (n·2 pi) is ultimately calculated, is preferably a quantity of the ultrasonic signal that is independent of the signal amplitude, e.g., the centroid of the received ultrasonic signal, the centroid of an envelope of the signal, or the point in time of another quantity that is independent of the signal amplitude. This has the advantage that the instant of receipt does not shift at different signal amplitudes.

According to a preferred embodiment of the present invention, the remainder (r(t)=n·2 pi) is determined based on the centroid of an envelope of the ultrasonic signal.

The remainder r(t) is preferably calculated as a function of the reception event ($t_s$), the phase angle (Δφ), and an offset value ($t_0$), i.e.: $r(t)=f(t_s, \Delta\phi, t_0)$.

The function f preferably includes a rounding function (e.g., "round"), which rounds a value to the next whole number.

According to a preferred embodiment of the present invention, the evaluation unit calculates a scattering parameter that indicates the extent of the rounding. The transit time calculation is particularly exact and robust when this scattering parameter is as small as possible. According to the present invention, it is therefore provided to regulate the scattering parameter to small values and to therefore adjust the offset value ($t_0$) accordingly. The offset value ($t_0$) is preferably varied when the absolute value of the scattering parameter—on average over time—exceeds a specified threshold.

The mean over time of the value of the scattering parameter (s) is preferably calculated within the framework of the scattering parameter regulation. As an alternative or in addition thereto, the mean over time of the scattering parameter (s) can be calculated.

The ultrasonic signals that were inverted using the reference timing signal or the phase-shifted reference timing signal are preferably sent to an integrator, which integrates the signal over several phases, preferably over the entire duration of the ultrasonic signal. The phase angle ($\Delta\phi$) is then preferably determined based on the output signals from the integrators. A filtering circuit can be provided in place of the integrators.

The ultrasonic signals, which are inverted in a segmented manner, are preferably also sent to a second pair of integrators, which integrate the signals over a period of the reference timing signal. Based on the output signals from these integrators, an envelope is preferably calculated, the centroid ($t_s$) of which represents the instant of receipt of the ultrasonic signal.

The ultrasonic flow sensor designed according to the present invention, with which the transit time of the ultrasonic sensors is calculated based on the phase angle ($\Delta\phi$) of a received signal relative to a reference timing signal, and with which a remainder (r(t)) is calculated, includes at least one ultrasonic converter for transmitting and/or receiving ultrasonic signals, an oscillator connected with the ultrasonic converter, which generates a timing signal, and a control and evaluation unit. According to the present invention, the evaluation unit includes a device (a circuit or software) that determines the phase angle ($\Delta\phi$) of the ultrasonic signal using the quadrature demodulation scheme—according to which a received ultrasonic signal with the frequency of the timing signal or a timing signal shifted by pi/2 is inverted in a segmented manner—and a device (a circuit or software) that determines a reception event, e.g., the centroid of an envelope, and, based on this, calculates the remainder (r(t)).

The control and evaluation unit is also designed such that one or more of the aforementioned functions can be carried out.

The invention is explained in greater detail below with reference to the attached drawing.

DESCRIPTION OF THE PREFERRED EMBODIMENTS

Figure 1:
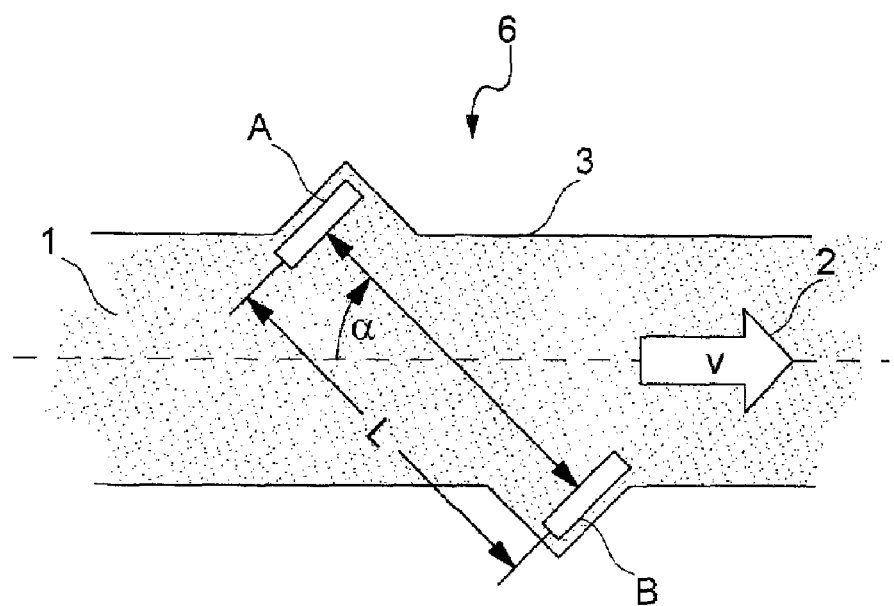
FIG. 1 shows an ultrasonic flow sensor with two ultrasonic converters according to the related art.
Figure 2:
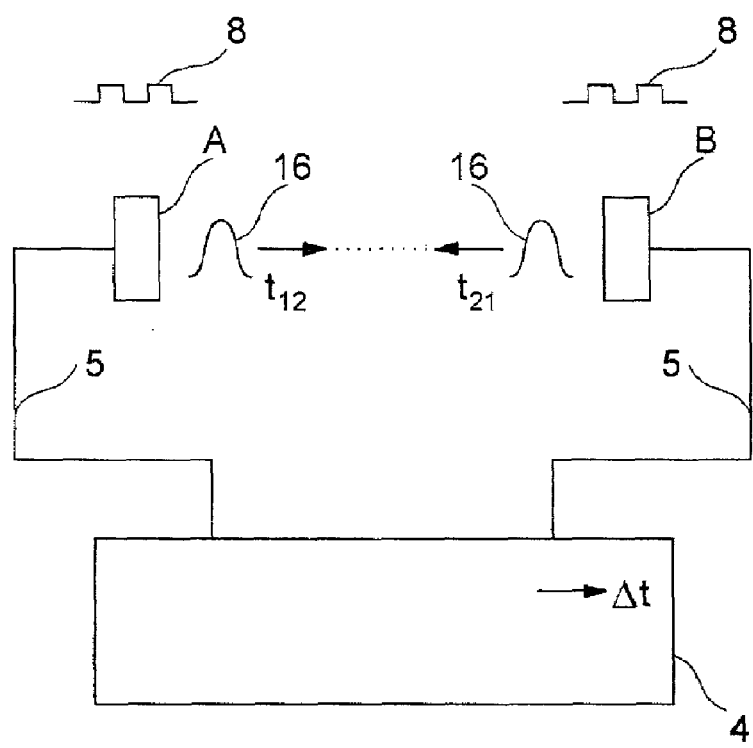
FIG. 2 shows an ultrasonic flow sensor with associated control and evaluation electronics.
Figure 3:
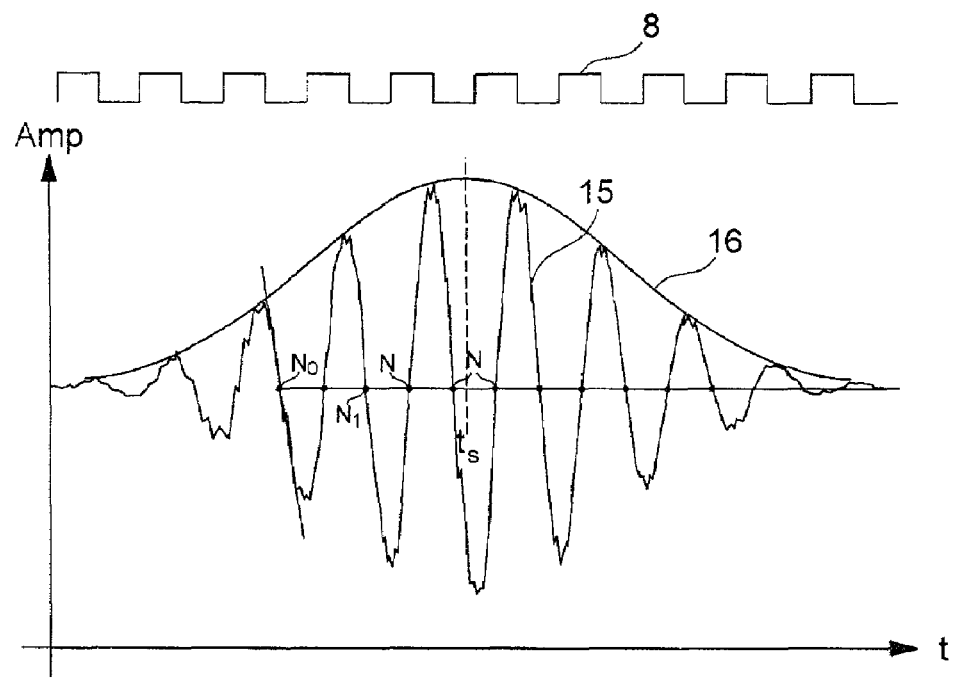
FIG. 3 shows the graph of a single ultrasonic signal, with its envelope.

FIGS. 1 through 3 are explained in the introduction of the description.

Figure 4:
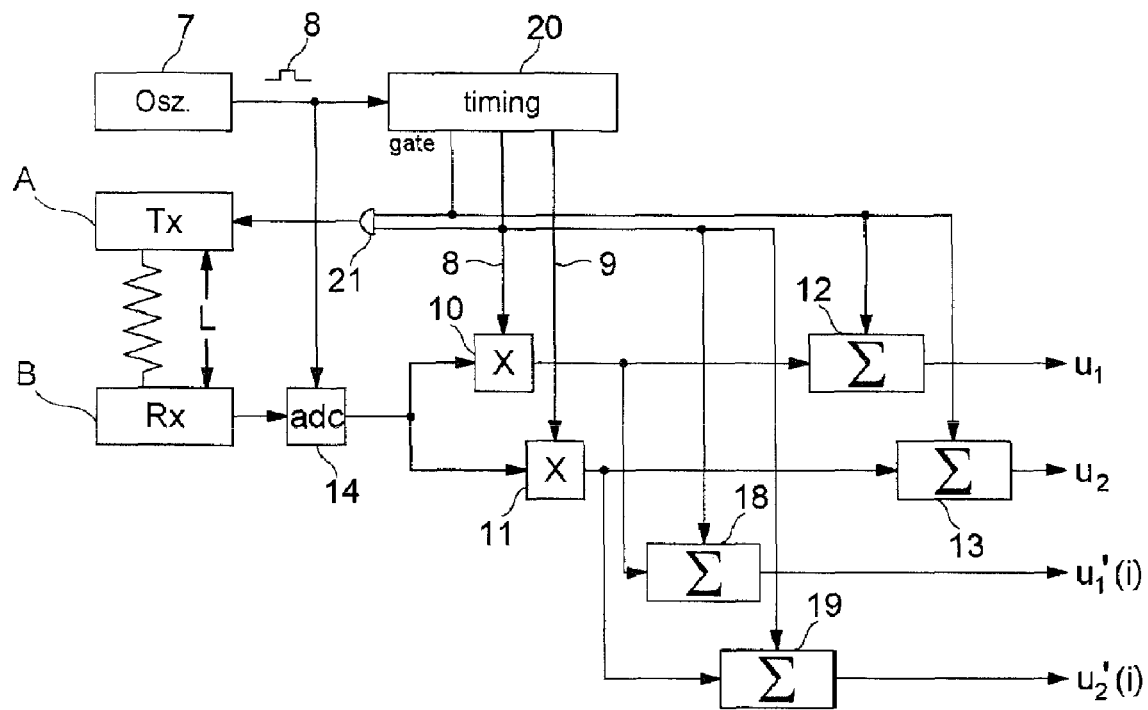
FIG. 4 shows a special embodiment of an ultrasonic flow sensor with evaluation electronics, which functions using the quadrature demodulation scheme.

FIG. 4 shows an embodiment of an ultrasonic flow sensor 6 with two ultrasonic converters A, B and control and evaluation electronics 4. Electronics 4 include an oscillator 7 that generates a timing signal 8, with which converters A, B are excited. As a result, both converters A generate ultrasonic signals 15, which are transmitted to the other converter, where they are detected. Based on transit time $t_{12}$ of a signal 15 in one direction, and transit time $t_{21}$ in the other direction, it is then possible to calculate the flow rate v or mass flow of flowing medium 1.

Transit time t of an ultrasonic signal 15 can also be depicted as a phase, i.e.:

$$t \sim n \cdot 2pi + \Delta\phi$$

or $$t \sim r(t) + \Delta\phi$$

Here, $\Delta\phi$ is the phase angle of received ultrasonic signal 15 relative to a reference timing signal 8, and n·2 pi and r(t) are the remainder of the entire phase; n is the number of complete wave trains within transit time t.

In this case, phase angle $\Delta\phi$ is determined with the quadrature demodulation scheme using two integrators 12, 13. (The quadrature demodulation scheme could also be realized, as an alternative and in an analogous manner, e.g., using inverting or non-inverting amplifiers.) The remainder (r(t)) is calculated based on a quantity that characterizes ultrasonic signal 15, e.g., the instant of receipt of the centroid of envelope 16.

To determine phase angle $\Delta\phi$, electronics 4 include an A/D converter 14, which which received signal 15 is digitized, and additional elements 10-13, which are explained below. The digitized received signal is divided into two signal paths and, depending on the state of a reference timing signal 8 or a reference timing signal 9 shifted by pi/2 (90°) phases, it is forwarded unchanged or it is inverted. The digitized received signal is forwarded unchanged, e.g., in the "high" state, and it is inverted in the "low" state. Reference timing signal 8 and timing signal 9 shifted by pi/2 are generated by a unit 20 based on oscillator timing signal 8. Forwarding digitized received signal 15 unchanged or inverting it corresponds to multiplication by +1 and −1. The associated signal operation is therefore depicted using two multipliers 10, 11.

The signals, which are inverted in a segmented manner, are then sent to two downstream integrators 12 and 13, which integrate the signals over their entire signal duration. (Low-pass filtering could be used instead of integration.)

Figure 5A:
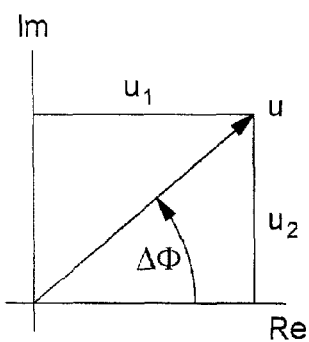
FIG. 5a shows a diagram that depicts the calculation of the phase angle

The two integral values $u_1$ and $u_2$ represent components of a vector u, the angle of which in the coordinate system is phase angle $\Delta\phi$. FIG. 5a shows vector u and components $u_1$, $u_2$, and angle $\Delta\phi$. Electronics, e.g., a microcontroller (not shown), are used to evaluate signals u, u'.

Figure 5B:
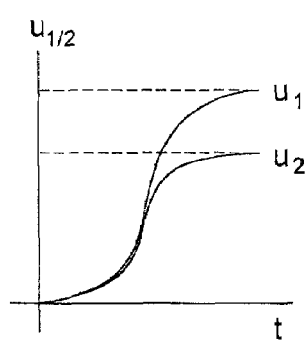
FIG. 5b shows the graph of output signals from the integrators in FIG. 4.

FIG. 5b shows the integration over time for an ultrasonic signal 15. Phase angle $\Delta\phi$ can be calculated based on the final values $u_1$, $u_2$ using a trigonometric function, e.g., arctan ($u_1/u_2$) or atan 2 ($u_1$, $u_2$). The following relationship is preferably used:

$$\Delta\phi = atan\ 2\ (u_1, u_2)$$

This function is not unequivocal and is periodically modulo 2 pi.

Figure 5C:
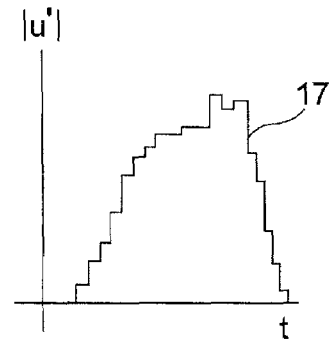
FIG. 5c shows the graph of an envelope calculated based on the ultrasonic signal.

Remainder (r(t)=n·2 pi, with n being a whole number) is calculated based on centroid $t_s$ of envelope of ultrasonic signal 15. (Another quantity that is independent of the signal amplitude could also be used). To this end, the signals—which have been digitized and inverted in a segmented manner—are sent to an integrator 18 or 19, and they are integrated over one period of reference timing signal 8. Every period is integrated individually, starting at zero. Output signals $u_1'(i)$ and $u_2'(i)$ result in envelope 17 shown in FIG. 5c. Integrators 18 and 19 are connected with multipliers 10 and 11 and are synchronized with reference timing signal 8. i is a counter for the particular period of ultransonic signal 15.

Using envelope 17, centroid $t_s$ is now determined, as the characteristic instant. Characteristic instant $t_s$ is a rough measure of the total transit time $t_{mes}$ of the ultrasonic signal. The following equation, e.g., can be used for centroid $t_s$:

$$t_s = 2pi \cdot \sum_{i=1}^{n} i \cdot h(i) \Big/ \sum_{i=1}^{n} h(i),$$

where $h(i) = u_1'(i)^2 + u_2'(i)^2$. To reduce the number of computational steps ($u_1$, $u_2$) and to over-proportionally weight greater signal amplitudes, the squared envelope $h(i)$ is used instead of the envelope.

Due to the modulo 2 pi ambiguity of phase angle $\Delta\phi$=atan 2 ($u_1$, $u_2$) mentioned above, the total transit time would have a sawtooth shape compared to the flow rate. To obtain a continuous linear characteristic curve for the transit time, a step function r(t) must be added to phase angle $\Delta\phi$ that was measured. It is important that the jumps in step function r(t) always take place simultaneously with the jumps in sawtooth curve $\Delta\phi(t)$. Desired remainder r(t) can be derived, e.g., from a quantity $t_{rest}$ (remaining transit time), as follows:

$r(t)=f(t_{rest})$, with $t_{rest}=t_s-\Delta\phi+t_0$

Here, $t_0$ is a constant offset value that will be explained in greater detail below. This remaining transit time $t_{rest}$ is a rough measure of the total transit time t of ultrasonic signal 15 minus exact phase shift $\Delta\phi$.

Although function $t_{rest}(t)$ appears to be stepped, it is superposed with noise caused by interfering signals, turbulences or changes in the shape of the envelope. Step function r(t) is therefore not defined directly by $t_{rest}(t)$, but rather preferably using a rounding function, i.e.:

$r(t)=2pi\cdot$round $(t_{rest}(t)/2pi)$.

The "round" function is a rounding function, which rounds a numerical value up or down to the next whole number.

The following should be noted with regard for offset value $t_0$: When remaining transit time $t_{rest}$ takes on values that are located directly on the limit of the rounding function (between rounding up and rounding down), remainder r(t) may jump. To prevent a signal jump, offset value $t_0$ is therefore chosen such that the extent of the rounding in function r(t)—on average over time—is as low as possible. To determine the extent of the rounding, a scattering parameter s is defined as:

$s=g(t_s, t_0, \Delta\phi)=$round$(t_{rest}/2pi)-t_{rest}/2pi$.

Scattering parameter s therefore indicates the extent to which rounding is carried out, and how far $t_{rest}$ is from ideal step function r(t). A favorable offset value $t_0$ has been chosen when |s|—on average over time, over several transit-time measurements—is as small as possible. In this case, rounding up and rounding down are carried out nearly exactly the same number of times.

Due to changes in the damping parameters of ultrasonic converters A, B, envelope 17 can change over time. This, in turn, can result in signal jumps. It is therefore provided that offset parameter $t_0$ is varied and that scattering parameter s is regulated to the smallest possible values. It can be provided to compare the mean of |s| over time with a specified threshold value $s_{max}$, and to change offset parameter $t_0$ when the mean of |s| over time exceeds threshold value $s_{max}$. Threshold value $s_{max}$ can be set, e.g., at $s_{max}$=0.3. The mean of |s| could also be regulated to a minimum (toward zero).

Figure 6:
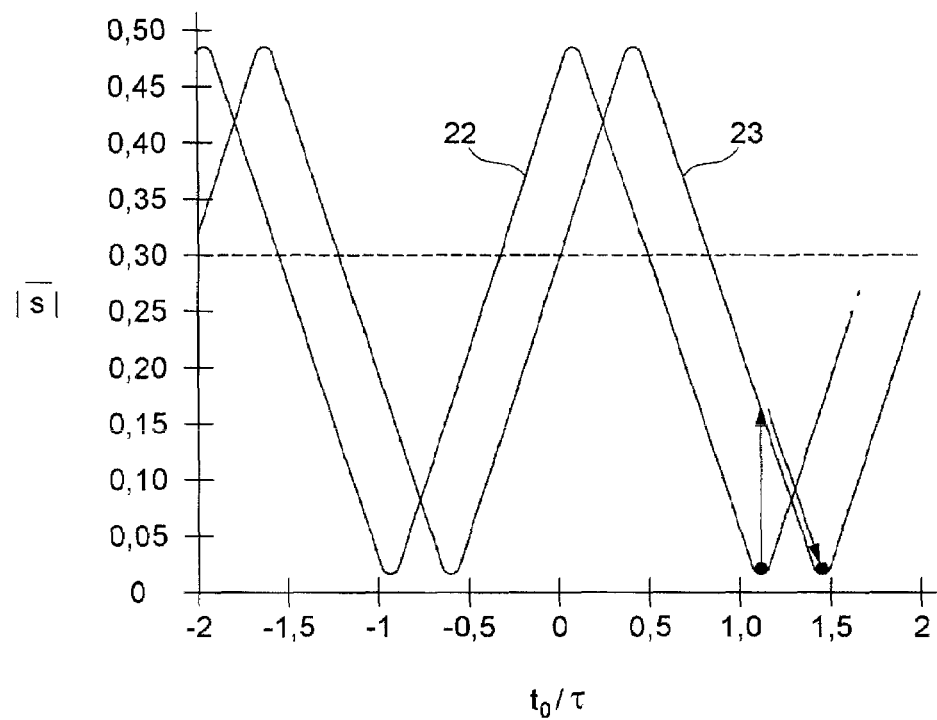
FIG. 6 shows the mean over time of a scattering parameter |s| as a function of offset value $t_0$.

FIG. 6 shows the graph of the mean of |s| over time. Curve 22 represents an earlier state, and curve 23 represents a later state, in which the shape of envelope 17 changed. With curve 23, the mean of |s| over time rises to a higher value, as indicated by arrow A. During regulation, offset value $t_0$ is now changed such that the mean of scattering parameter |s| over time becomes minimal (see arrow b).

Figure 7:
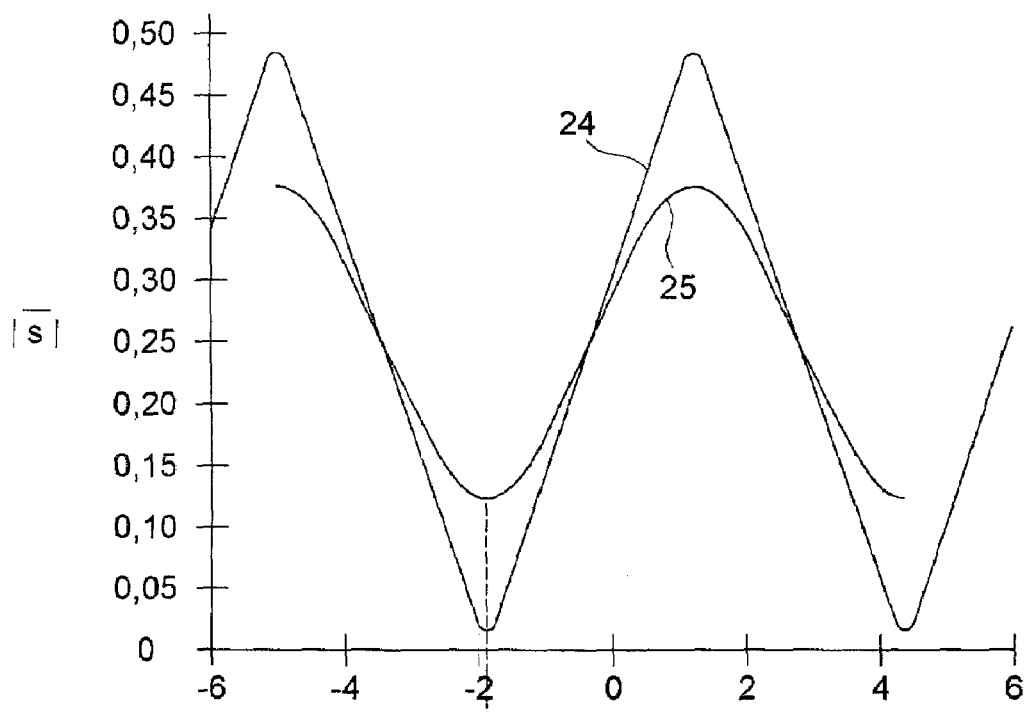
FIG. 7 shows the graph of the scattering parameter |s| as a function of offset value $t_0$ with different signal interferences.
Figure 8:
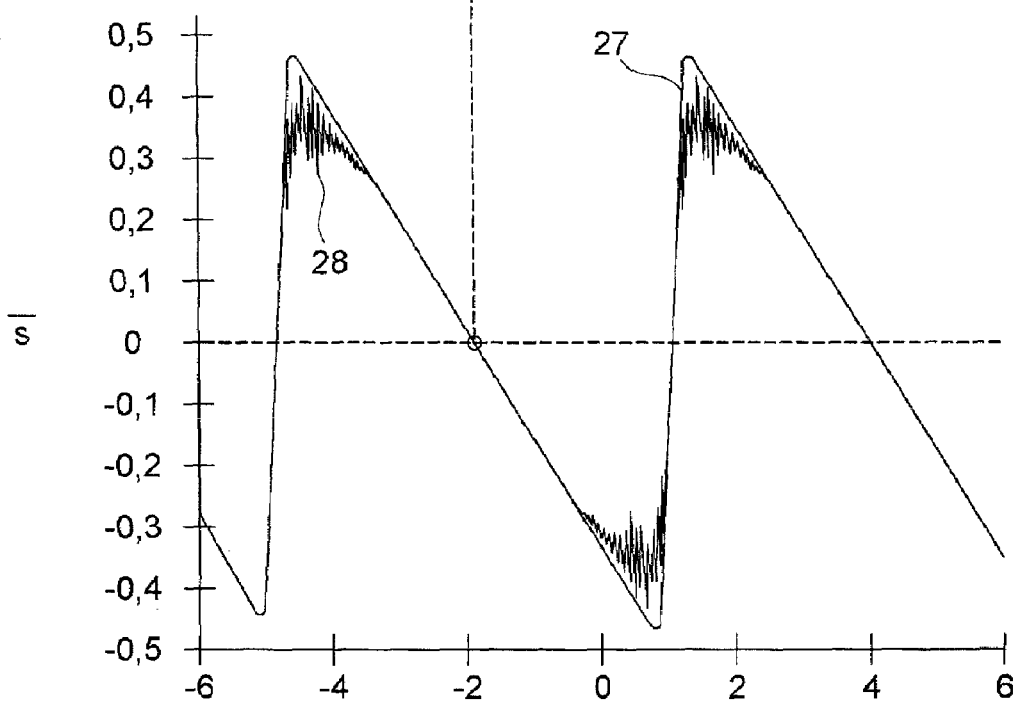
FIG. 8 shows the graph of the mean scattering parameter s as a function of offset value $t_0$ with interferences of different intensities.

FIG. 7a shows the graph of the mean of |s| for disturbing influences with different intensities. Curve 24 represents a state with relatively weak signal interferences, and curve 25 represents a state with strong signal interferences. As shown, the minima of curve 25 are not as sharply bent, and are therefore defined less exactly.

FIG. 7b shows the corresponding curves for the graph of mean $\bar{s}$ over time with weak signal disturbances (curve 27) and strong signal disturbances (curve 28).

In the regions of the minimas of curve 25, $\bar{s}$ is linearly dependent on offset parameter $t_0$ and is influenced very little by the intensity of the signal disturbances. In this case, the best strategy for regulation is to vary offset parameter $t_0$ such that $\bar{s}$=0. The mean of absolute value |s| over time is still required, however, in order to enter this range of regulation at all. If, e.g., |$\bar{s}$| is a maximum, then $\bar{s}$=0 as well, but a poor choice was made for offset value $t_0$. To take this into account, an initial check can be carried out, e.g., to determine whether |$\bar{s}$| is greater than a specified threshold, e.g., |$\bar{s}$|>0.25. If so, mean |$\bar{s}$| can be brought into a range |$\bar{s}$|≦0.25 immediately by changing $t_0$ by +−¾·pi. The change of $t_0$ must take place in the positive direction if |$\bar{s}$|≦0 ist, and in the negative direction if |$\bar{s}$|>0.

If mean |$\bar{s}$| is less than the threshold value, e.g., |$\bar{s}$|≦0.25, then $t_0$ is replaced with $t_0-2pi\cdot|\bar{s}|$. In this manner, |$\bar{s}$| is always reset immediately to the next closest minimum, without inducing any regulation oscillations.

LIST OF REFERENCE NUMERALS

1 Flowing fluid
2 Direction of flow
3 Pipeline
4 Control and evaluation unit
5 Converter output signal
6 Ultrasonic flow system
7 Oscillator
8 Timing signal
9 Phase-shifted timing signal
10 Multiplier
11 Multiplier
12 Integrator
13 Integrator
14 A/D converter
15 Ultrasonic signal
16 Envelope
17 Calculated envelope
18 Integrator
19 Integrator
20 Timing unit 21 OR gate
22 Curve shape of |s̄| in the initial state
23 Curve shape of |s̄| in the changed state
24 Shape of |s̄| with minimal interferences
25 Shape of |s̄| with strong interferences
27 Shape of s̄ with minimal interferences
28 Shape of s̄ with strong interferences
L Measurement path
A, B Ultrasonic converters
$t_s$ Centroid of the envelope

What is claimed is:

1. A method for determining the transit time (t) of an ultrasonic signal (15) from an ultrasonic sensor (6) that was launched into a measurement path (L) by an ultrasonic converter (A, B); the phase shift ($\Delta\phi$) of the ultrasonic signal (15) is determined relative to a reference timing signal (8), and a remainder (r(t)) is determined as a measure of the transit time (t) of the ultrasonic signal (15),
wherein
the phase shift ($\Delta\phi$) is determined using a quadrature demodulation scheme, with which the received ultrasonic signal (15) is inverted, in a segmented manner, using a timing signal (8) and a phase-shifted timing signal (9), and
the remainder (r(t)) is determined based on a characteristic quantity ($t_s$) of the ultrasonic signal (15).

2. The method as recited in claim 1,
wherein
the remainder (r(t)) is determined based on a quantity of the ultrasonic signal (15) that is independent of the amplitude of the received ultrasonic signal (15).

3. The method as recited in claim 1,
wherein
the remainder (r(t)) is a function of the characteristic quantity ($t_s$) of the phase shift ($\Delta\phi$) and an offset value ($t_o$).

4. The method as recited in claim 3,
wherein
the offset value ($t_o$) is variable.

5. The method as recited in claim 1,
wherein
the remainder (r(t)) includes a rounding function.

6. The method as recited in claim 5,
wherein,
a scattering parameter (s) is calculated, which represents the extent of the rounding.

7. The method as recited in claim 6,
wherein,
the scattering parameter (s) is regulated to a small value.

8. The method as recited in claim 7,
wherein,
during rounding, the mean over time of the scattering parameters (s) of several consecutive measurements is calculated.

9. The method as recited in claim 1,
wherein
the ultrasonic signals (15) that were inverted in a segmented manner are integrated using an integrator (18, 19); every period of the timing signal (8) is integrated individually, and the remainder (r(t)) is determined based on the output signals from the integrators (18, 19).

10. An ultrasonic sensor, particularly for determining the flow rate (v) of a medium (1) flowing through a pipeline (3), including at least one ultrasonic converter (A, B) for transmitting and/or receiving ultrasonic signals (15), an oscillator connected with the ultrasonic converter (A, B), and an evaluation unit (4) that determines a phase shift ($\Delta\phi$) of the received ultrasonic signal (15) relative to a timing signal (8) and a remainder (r(t)) as a measure of the transit time (t) of the ultrasonic signal (15),
wherein
the evaluation unit (4) includes a device (10-13) that determines the phase shift ($\Delta\phi$) using a quadrature demodulation scheme, and a device (18, 19) that determines a characteristic quantity ($t_s$), based on which the remainder (r(t)) of the transit time (t) is calculated.

11. Ultrasonic flow sensor as recited in claim 10,
wherein
the evaluation unit (4) determines the centroid ($t_s$) of an envelope (17) of the received ultrasonic signal (15).

12. The ultrasonic flow sensor as recited in claim 10,
wherein
the evaluation unit (4) includes an inverter (10, 11), which inverts the received ultrasonic signal (15)—in a segmented manner—using a timing signal or a phase-shifted timing signal (9), and a first integrator (12), to which the ultrasonic signal (15) inverted using the timing signal (8) is sent, and a second integrator (13), to which the ultrasonic signal (15) inverted using the phase-shifted timing signal (9) is sent.

13. The ultrasonic flow sensor as recited in claim 10,
wherein
the evaluation unit (4) includes an integrator (18), to which an ultrasonic signal (15) inverted using the timing signal (8) is sent, and an integrator (19) to which the ultrasonic signal (15) inverted using the phase-shifted timing signal (9) is sent; every period of the signal (15) is integrated individually.

14. The ultrasonic flow sensor as recited in claim 9,
wherein
the evaluation unit (4) calculates the remainder (r(t)) as a function of the reception event ($t_s$), the phase shift ($\Delta\phi$), and an offset value ($t_o$).

15. The ultrasonic flow sensor as recited in claim 10,
wherein
the evaluation unit (4) calculates the remainder (r(t)) with a rounding function.

16. The ultrasonic flow sensor as recited in claim 15,
wherein,
the evaluation unit (4) calculates a scattering parameter (s), which represents the extent of the rounding.

17. The ultrasonic flow sensor as recited in claim 16,
wherein,
the evaluation unit (4) regulates the scattering parameter (s).

* * * * *